(12) United States Patent
Cantrell

(10) Patent No.: US 10,987,241 B1
(45) Date of Patent: Apr. 27, 2021

(54) SUPRAPUBIC REGION COMPRESSION PLATE AND RELATED METHODS

(71) Applicant: David Wayne Cantrell, Trinity, AL (US)

(72) Inventor: David Wayne Cantrell, Trinity, AL (US)

( * ) Notice: Subject to any disclaimer, the term of this patent is extended or adjusted under 35 U.S.C. 154(b) by 163 days.

(21) Appl. No.: 16/284,940

(22) Filed: Feb. 25, 2019

Related U.S. Application Data

(63) Continuation-in-part of application No. 15/080,659, filed on Mar. 25, 2016, now Pat. No. 10,213,332.

(60) Provisional application No. 62/138,096, filed on Mar. 25, 2015, provisional application No. 62/164,097, filed on May 20, 2015.

(51) Int. Cl.
*A61F 5/41* (2006.01)
*A61F 5/00* (2006.01)

(52) U.S. Cl.
CPC ............. *A61F 5/41* (2013.01); *A61F 5/0009* (2013.01); *A61F 2005/414* (2013.01)

(58) Field of Classification Search
CPC .... A61F 5/41; A61F 5/0009; A61F 2005/414; A61F 5/03
USPC .......................................................... 600/38
See application file for complete search history.

(56) References Cited

U.S. PATENT DOCUMENTS

| | | |
|---|---|---|
| 4,203,432 A | 5/1980 | Koch |
| 4,440,183 A | 4/1984 | Miller |
| 4,488,541 A | 12/1984 | Garcia |
| 4,724,829 A * | 2/1988 | Knapps ............ A61F 5/41 600/41 |
| 5,728,043 A * | 3/1998 | Yong ............... A61F 5/41 600/39 |
| 6,139,515 A | 10/2000 | Ito |
| D480,145 S | 9/2003 | Slautterback |
| 7,341,553 B2 | 3/2008 | Egretier |
| 8,109,569 B2 | 2/2012 | Mitchell |
| 8,109,869 B2 * | 2/2012 | Beaulieu ......... A61H 19/34 600/38 |
| 8,360,957 B2 | 1/2013 | Kuri |
| 8,974,369 B2 | 3/2015 | Tomlinson, Jr. |

(Continued)

FOREIGN PATENT DOCUMENTS

| | | |
|---|---|---|
| CA | 2100370 | 1/1994 |
| CA | 2503233 | 7/2006 |

(Continued)

OTHER PUBLICATIONS

Oxford Living Dictionaries, definition of bar, printed from https://en.oxforddictionaries.com/definition/bar, Jun. 25, 2018.

*Primary Examiner* — Samuel G Gilbert
(74) *Attorney, Agent, or Firm* — Bryan Cave Leighton Paisner LLP

(57) ABSTRACT

A compression plate for compressing a suprapubic region of a user. The compression plate can include a base portion and an upper portion positioned above the base portion. The upper portion can include a left-side upper arm, a right-side upper arm, and a notch positioned between the left- and right-side upper arms. The notch can be configured to receive a penis of the user. The base portion and the upper portion can be contoured to apply pressure to and compress the suprapubic region of the user such that a measurable, visible, or usable length of the penis is increased. Other embodiments are described.

16 Claims, 9 Drawing Sheets

(56) References Cited

U.S. PATENT DOCUMENTS 10,213,332 B1    2/2019   Cantrell
2006/0142638 A1*   6/2006   Flores ...................... A61F 5/41
                                                                             600/38

FOREIGN PATENT DOCUMENTS

CN           2751792      1/2006
DE     202015002335      6/2015

* cited by examiner

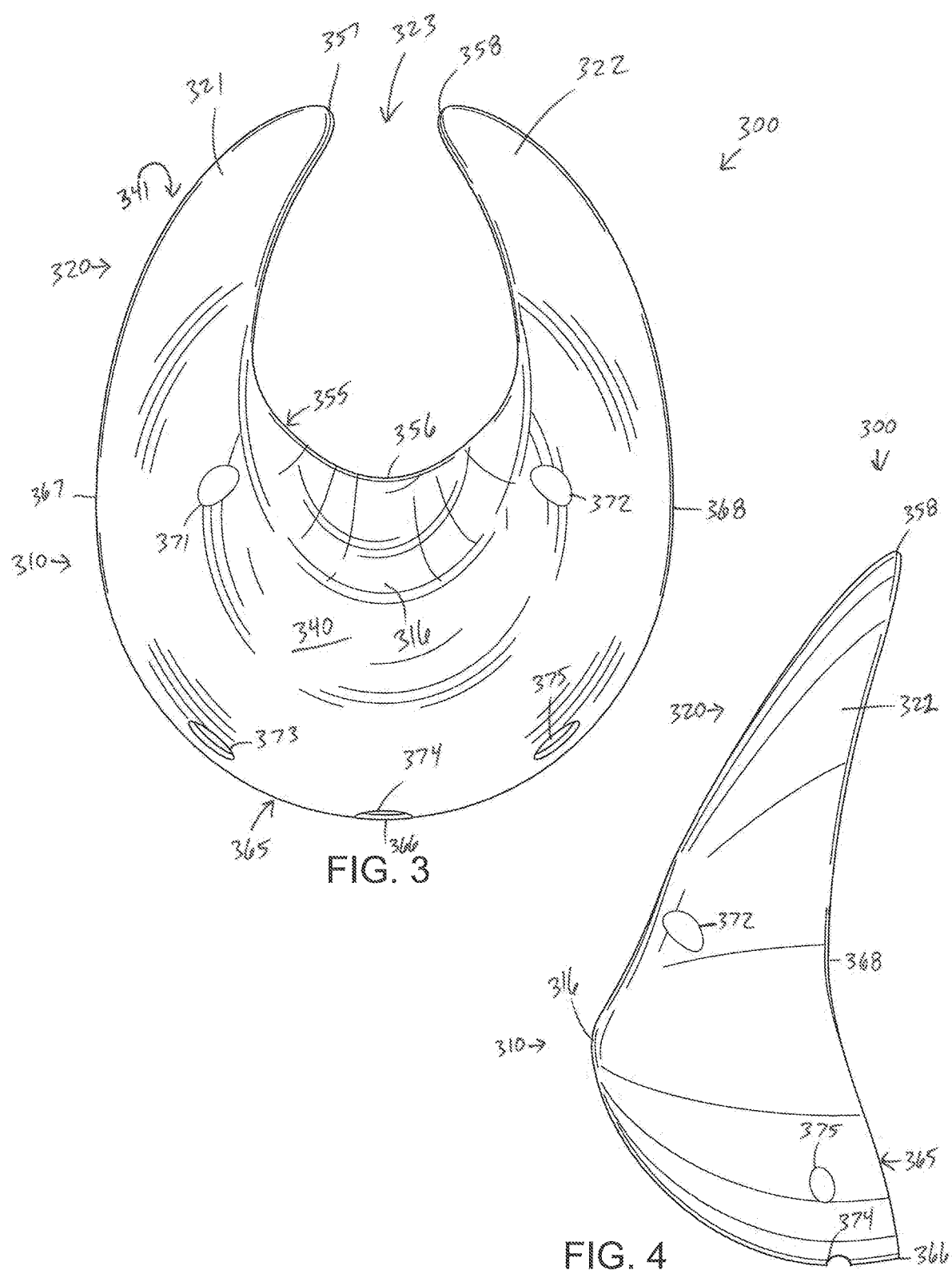

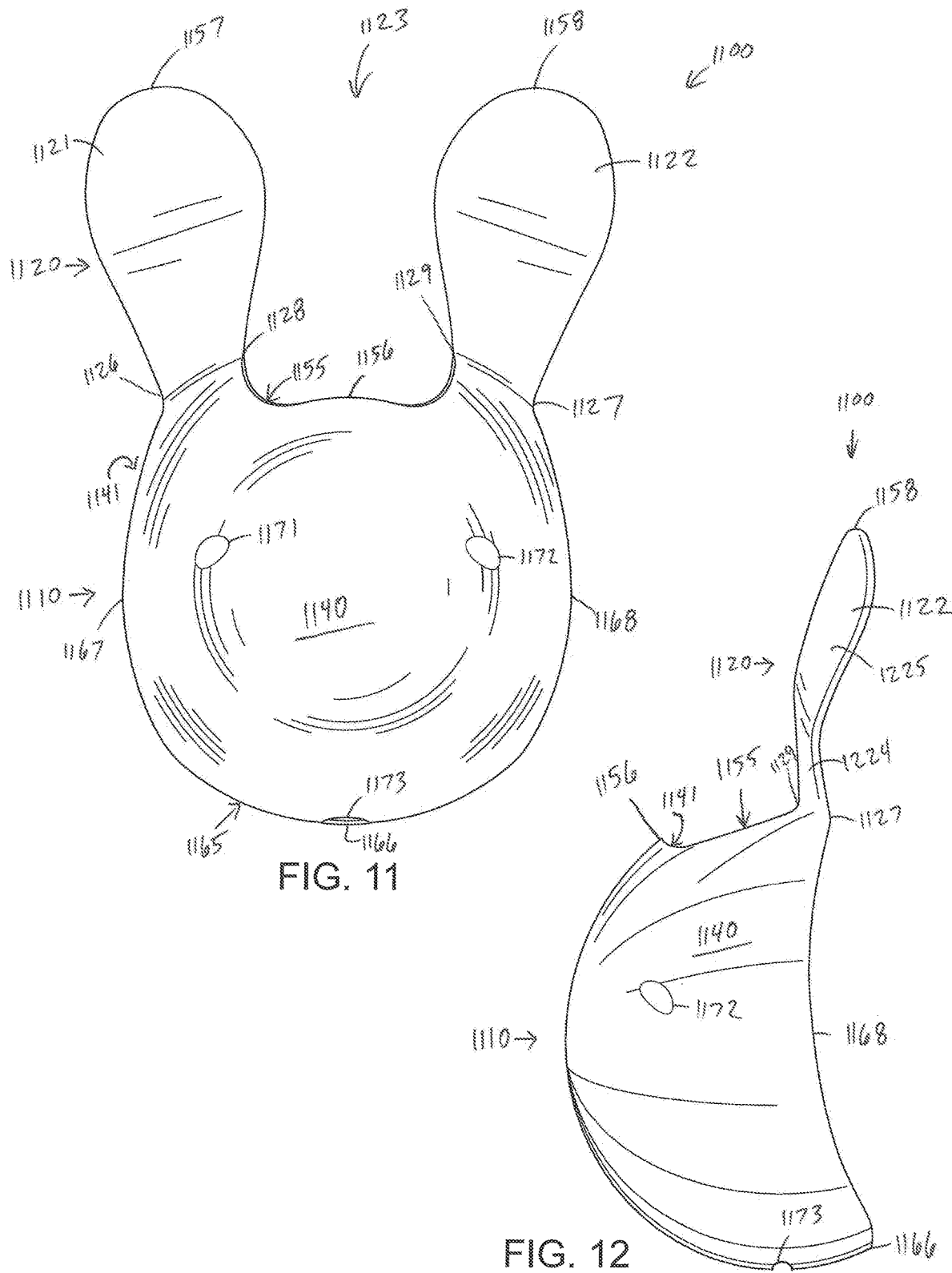

SUPRAPUBIC REGION COMPRESSION PLATE AND RELATED METHODS

CROSS-REFERENCE TO RELATED APPLICATIONS

This application is a continuation-in-part of U.S. patent application Ser. No. 15/080,659, filed Mar. 25, 2016, which claims the benefit of U.S. Provisional Application No. 62/138,096, filed Mar. 25, 2015, and U.S. Provisional Application No. 62/164,097, filed May 20, 2015. U.S. patent application Ser. No. 15/080,659 and U.S. Provisional Application Nos. 62/138,096 and 62/164,097 are incorporated herein by reference in their entirety.

BACKGROUND

The length of a man's penis is important for the pleasure of both partners during sex and for the man's confidence and self-image. Aging and/or weight gain can cause an increase in volume or size of the fatty tissue in the pelvic hypogastric or suprapubic region, directly above the penis. This increase in fatty tissue causes a resulting decrease in the measurable, visible, or usable length of the penis extending from the suprapubic region. To permanently increase the measurable, visible, or usable length of the penis, some men undergo suprapubic region fat pad reduction surgery, which can be costly, painful, and requires recovery time. Accordingly, there is a need for a non-surgical, temporary assembly and method to address challenges presented by pelvic hypogastric or suprapubic region fatty tissue and having the performance, cost, comfort, and other features desired by consumers.

SUMMARY

A number of embodiments include a compression plate for compressing a suprapubic region of a user. The compression plate can include a base portion and an upper portion positioned above the base portion. The upper portion can include a left-side upper arm, a right-side upper arm, and a notch positioned between the left- and right-side upper arms. The notch can be configured to receive a penis of the user. The base portion and the upper portion can be contoured to apply pressure to and compress the suprapubic region of the user such that a measurable, visible, or usable length of the penis is increased.

Additional embodiments include a method of compressing a suprapubic region of a user to increase a measurable, visible, or usable length of a penis of the user. The method can include positioning a compression plate such that an inner surface of the compression plate engages the suprapubic region of the user and the penis of the user is adjacent to a notch of the compression plate. The compression plate can include a base portion and an upper portion positioned above the base portion. The upper portion can include the notch. The method also can include securing the compression plate to the suprapubic region of the user using at least one of a belt, a harness, one or more straps, or an undergarment to force the base portion and the upper portion against the suprapubic region of the user, thereby compressing the suprapubic region to increase a measurable, visible, or usable length of the penis.

Further embodiments include a method of providing a compression plate for compressing a suprapubic region of a user. The method can include providing a base portion. The method also can include providing an upper portion positioned above the base portion. The upper portion can include a left-side upper arm, a right-side upper arm, and a notch positioned between the left- and right-side upper arms. The notch can be configured to receive a penis of the user. The base portion and the upper portion can be contoured to apply pressure to and compress the suprapubic region of the user such that a measurable, visible, or usable length of the penis is increased.

Other embodiments and features will be in part apparent and in part pointed out hereinafter.

BRIEF DESCRIPTION OF THE DRAWINGS

To facilitate further description of the embodiments, the following drawings are provided in which:

FIG. 3 illustrates a front view of a compression plate, according to another embodiment;

FIG. 4 illustrates a right side view of the compression plate of FIG. 3;

FIG. 11 illustrates a front view of a compression plate, according to another embodiment;

FIG. 12 illustrates a right side view of the compression plate of FIG. 11;

Figure 1:
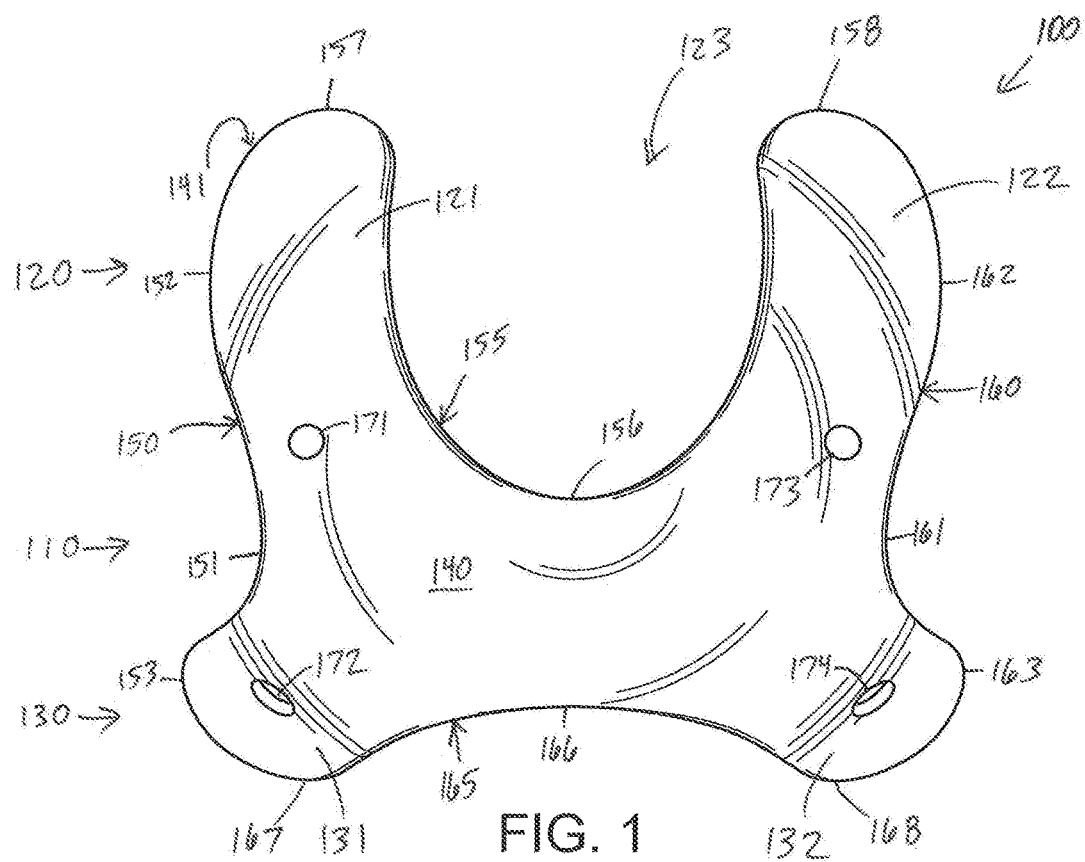
FIG. 1 illustrates a front view of a compression plate, according to an embodiment.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order.

It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The orientation of the compression plate in the drawings provides the point of reference for the terms defining relative locations and positions of structures and components of the compression plate, including but not limited to the terms "upper," "lower," "above," below," "left," and "right," as used throughout the present disclosure.

The terms "couple," "coupled," "couples," "coupling," and the like should be broadly understood and refer to connecting two or more elements mechanically and/or otherwise. As defined herein, two or more elements are "integral" if they are comprised of the same piece of material. As defined herein, two or more elements are "non-integral" if each is comprised of a different piece of material.

DETAILED DESCRIPTION

Figure 2:
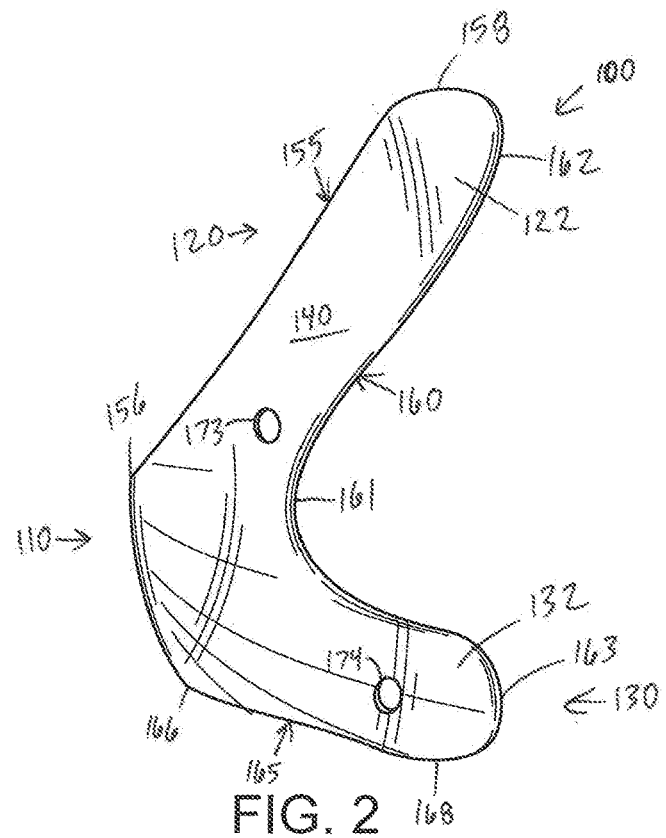
FIG. 2 illustrates a right side view of the compression plate of FIG. 1.

Turning to the drawings, FIG. 1 illustrates a front view of a compression plate 100. FIG. 2 illustrates a right side view of compression plate 100. Compression plate 100 is merely exemplary, and embodiments of the compression plate are not limited to embodiments presented herein. The compression plate can be employed in many different embodiments or examples not specifically depicted or described herein. In some embodiments, compression plate 100 can be similar to various compression plates shown and described in U.S. patent application Ser. No. 15/080,659 ("the '659 application"), and various components of compression plate 100 can be similar or identical to various components of the compression plates shown and described in the '659 application. Compression plate 100 can be configured to compress a suprapubic region of a user. Compression plate 100 can be configured to be removably attached to a user such that the compression plate 100 engages the suprapubic region of the user for compression thereof. Compression plate 100 can be rigid or semi-rigid such that compression plate 100 is configured to exert pressure on the suprapubic region to compress the suprapubic region. In some embodiments, compression plate 100 is rigid. For example, compression plate 100 may be made of a rigid plastic, metal, or other suitable material. In other embodiments, compression plate 100 can be made of a semi-rigid plastic, rubber, or other suitable material. In some embodiments, compression plate 100 can be made of a rigid to semi-rigid, durable, injection molded or otherwise moldable medical grade polymer.

Referring to FIGS. 1-2, compression plate 100 can include a base portion, such as base portion 110, an upper portion, such as upper portion 120, and/or a lower portion, such as lower portion 130. In other embodiments, the compression plate does not include a lower portion. In many embodiments, base portion 110, upper portion 120, and lower portion 130 can be integral, such as a one-piece, unitary construction. In other embodiments, base portion 110, upper portion 120, and lower portion 130 can be separate pieces that are coupled together, either removably or non-removably. Upper portion 120 can be positioned above and adjacent to base portion 110. Upper portion 120 can include a left-side upper arm 121, a right-side upper arm 122, and a notch 123 positioned between left-side upper arm 121 and right-side upper arm 122. Notch 123 can be configured to receive a penis of the user. Lower portion 130 can be positioned below and adjacent to base portion 110. Lower portion 130 can include a left-side lower arm 131 and a right side lower arm 132, which can each extend below base portion 110.

Compression plate 100 can include an outer surface 140 and an inner surface 141 opposite outer surface 140. Outer surface 141 can face away from the user during use of compression plate 100. Inner surface 141 can face toward the user during use of compression plate 100 and engages the suprapubic region of the user.

Compression plate 100 can include a left edge 150, which can extend between a left region 152 of left-side upper arm 121 and a left region 153 of left-side lower arm 131. Between left region 152 of left-side upper arm 121 and left region 153 of left-side lower arm 131, left edge 150 can extend rightward to a left inlet region 151 of base portion 110, which can be located rightward of left region 152 and left region 153. Compression plate 100 can include a right edge 160, which can extend between a right region 162 of right-side upper arm 122 and a right region 163 of right-side lower arm 132. Between right region 162 of right-side upper arm 122 and right region 163 of right-side lower arm 132, right edge 160 can extend leftward to a right inlet region 161 of base portion 110, which can be located leftward of right region 162 and right region 163. Compression plate 100 can include an upper edge 155, which can extend between a top region 157 of left-side upper arm 121 and a top region 158 of right-side upper arm 122. Between top region 157 of left-side upper arm 121 and top region 158 of right-side upper arm 122, upper edge 155 can descend to a recess region 156. Recess region 156 can be located below top region 157 and top region 158, at a bottom of notch 123, and/or centered between the left and right sides of compression plate 100. Compression plate 100 can include a lower edge 165, which can extend between a bottom region 167 of left-side lower arm 131 and a bottom region 168 of right-side lower arm 132. Between bottom region 167 of left-side lower arm 131 and bottom region 168 of right-side lower arm 132, lower edge 165 can ascend to a raised region 166. Raised region 166 can be located above bottom region 167 and bottom region 168, and/or centered between the left and right sides of compression plate 100. In several embodiments, left edge 150 can connect with upper edge 155 between left region 152 and top region 157 of left-side upper arm 121 in a curvilinear and substantially rounded manner, right edge 160 can connect with upper edge 155 between right region 162 and top region 158 of right-side upper arm 122 in a curvilinear and substantially rounded manner, left edge 150 can connect with lower edge 165 between left region 153 and bottom region 167 of left-side lower arm 131 in a curvilinear and substantially rounded manner, and right edge 160 can connect with lower edge 165 between right region 163 and bottom region 168 of right-side lower arm 132 in a curvilinear and substantially rounded manner. In a number of embodiments, upper edge 155, lower edge 165, left edge 150, and/or right edge 160 can be curvilinear.

In a number of embodiments, compression plate 100 can be smaller in height in the center of compression plate 100 than at the left and right sides of compression plate. For example, the height between recess region 156 and raised region 166 of compression plate 100 can be smaller than the height of compression plate 100 between top region 157 of left-side upper arm 121 and bottom region 167 of left-side lower arm 131, and can be smaller than the height of compression plate 100 between top region 158 of right-side upper arm 122 and bottom region 168 of right-side lower arm 132. In several embodiments, compression plate 100 can be narrower in width at a base portion 110 than at upper portion 120 and/or lower portion 130. In a number of embodiments, base portion 110 can be narrower in width than at least a portion of upper portion 120 and at least a portion of lower portion 130. For example, a width between left inlet region 151 and right inlet region 161 of base portion 110 can be narrower than a width between left region 152 of left-side upper arm 121 and right region 162 of right-side upper arm 122, and can be narrower than a width between left region 153 of left-side lower arm 131 and right region 163 of right-side lower arm 132. In many embodiments, left-side upper arm 121 and right-side upper arm 122 can each be longer than each of left-side lower arm 131 and right-side lower arm 132.

As shown in FIGS. 1-2, compression plate 100 can be curved or angled inward toward inner surface 141, such that at least a portion of inner surface 141 is concave and/or at least a portion of outer surface 140 is convex. For example, at least a portion of each of left-side upper arm 121, right-side upper arm 122, left-side lower arm 131, and right-side lower arm 132 can be curved or angled inward toward inner surface 141 relative to base portion 110. In many embodiments, the left side of compression plate 100 and the right side of compression plate 100 can be curved or angled inward toward inner surface 141 relative to the center of compression plate 110 between the sides of compression plate 110 (e.g., inner surface 141 is concave in the horizontal direction). For example, left inlet region 151 and right inlet region 161 can be positioned further rearward than a center of base portion 110, bottom region 167 and bottom region 168 can be positioned further rearward than raised region 166, and/or top region 157 and top region 158 can be positioned further rearward than recess region 156. In many embodiments, compression plate 100 can be curved and/or angled inward toward inner surface 141 along a vertical direction (e.g., inner surface 141 is concave in a vertical direction), such that raised region 166 can be positioned further rearward than recess region 156, left region 152 and left region 153 can be positioned further rearward than left inlet region 151, and/or right region 162 and right region 163 can be positioned further rearward than right inlet region 161.

The contouring, such as the curvature and/or angling of compression plate 100, and the curvilinear shape of upper edge 155, lower edge 165, left edge 150, and/or right edge 160, as described above, can permit compression plate 100 to generally conform to the anatomy of the user around the sides and underside of the base of the penis in the suprapubic region. Notch 123 can have an entrance facing upward and away from bottom portion 110. Notch 123 can have a substantially semicircular or "horseshoe" shaped opening. Notch 123 can be configured to receive the penis of the user, such that upper edge 155 can be surround the left and right sides and the underside of the base of the penis, with left-side upper arm 121 and right-side upper arm 122 positioned around the left and right sides of the base of the penis, respectively, when viewed from the outside. Recessed region 156 and/or bottom portion 110 can be positioned below the underside of the base of the penis. Base portion 110, upper portion 120, and/or lower portion 130 can be contoured to apply pressure to and compress the suprapubic region of the user such that a measurable, visible, or usable length of the penis is increased. For example, left-side upper arm 121 and right-side upper arm 122 can be configured to apply pressure to and compress a portion of the suprapubic region of the user at a left side and a right side of the base of the penis, and base portion 110 can be configured to apply pressure to and compress a portion of the suprapubic region of the user at an underside below the base of the penis. In a number of embodiments, base portion 110 and/or lower portion 130 can be configured to apply pressure to and compress at least a portion of a scrotum of the user. In several embodiments, at least a portion of the scrotum can be uncovered by compression plate 100.

In some embodiments, such as shown in FIGS. 1-2, compression plate 100 can include one or more mounting holes, such as mounting holes 171-174. In many embodiments, a belt, a harness, and/or one or more straps can be engaged (e.g., adhesive, hook-and-loop fasteners, molding, one or more clips, buckles, buttons, clasps, or another suitable attachment) with mounting holes 171-174 to create a compression assembly, similar to the suprapubic region compression assemblies shown and described in the '659 application. For example, the belts, harnesses, and/or straps shown and described in the '659 application can be used in conjunction with compression plate 100 to create a compression assembly that can secure compression plate 100 to the user. The belt, harness, and/or straps can be adjustable to accommodate users of different sizes and/or facilitate applying and tightening the compression assembly to the user. In other embodiments, an undergarment, such as a customized brief, can be used to secure compression plate 100 to the user. In many embodiments, the belts, harnesses, straps, and/or undergarments can be used to urge the compression plate toward the user to compress the suprapubic region of the user. In some embodiments when an undergarment is used, the compression plate can be devoid of mounting holes. As shown in FIGS. 1-2, there can be four mounting holes, such as mounting holes 171-174, which in some embodiments can be located at each quadrant of compression plate 100, such as a different one of mounting holes 171-174 at each of left-side upper arm 121, right-side upper arm 122, left-side lower arm 131, and right-side lower arm 132. In other embodiments, other positions of the mounting holes can be used, and/or compression plate 100 can include another number of mounting holes, such as two holes, six holes, or another suitable number.

Turning ahead in the drawings, FIG. 3 illustrates a front view of a compression plate 300. FIG. 4 illustrates a right side view of compression plate 300. Compression plate 300 is merely exemplary, and embodiments of the compression plate are not limited to embodiments presented herein. The compression plate can be employed in many different embodiments or examples not specifically depicted or described herein. In some embodiments, compression plate 300 can be similar to compression plate 100 (FIGS. 1-2), and various components and/or materials of compression plate 300 can be similar or identical to various components and/or materials of compression plate 100 (FIGS. 1-2). For example, compression plate 300 can include a base portion 310 and an upper portion 320, which can be similar to base portion 110 (FIG. 1) and upper portion 120 (FIG. 1), respectively. Upper portion 320 can include a left-side upper arm 321, a right-side upper arm 322, and a notch 323 positioned between left-side upper arm 321 and right-side upper arm 322. Left-side upper arm 321, right-side upper arm 322, and notch 323 can be similar to left-side upper arm 121 (FIG. 1), right-side upper arm 122 (FIG. 1), and notch 123 (FIG. 1), respectively. Compression plate 300 can include an outer surface 340 and an inner surface 341 opposite outer surface 340. Outer surface 340 and inner surface 341 can be similar to outer surface 140 (FIG. 1) and inner surface 141 (FIG. 1), respectively. Compression plate 300 can include mounting holes 371-575, which can be similar to mounting holes 171-174 (FIG. 1).

Compression plate 300 can be different from compression plate 100 (FIG. 1) in some aspects. For example, compression plate 300 can be devoid of a lower portion, such as lower portion 130 (FIG. 1), and can be devoid of the lower arms, such as left-side lower arm 131 (FIG. 1) and right-side lower arm 132 (FIG. 1). Compression plate 300 can include an upper edge 355 and a lower edge 365. Upper edge 355 can be similar to upper edge 155 (FIG. 1). For example, upper edge 355 can extend between a top region 357 of left-side upper arm 321 and a top region 358 of right-side upper arm 322. Between top region 357 of left-side upper arm 321 and top region 358 of right-side upper arm 322, upper edge 355 can descend to a recess region 356. Recess region 356 can be located below top region 357 and top region 358, at a bottom of notch 323, and/or centered between the left and right sides of compression plate 300.

Lower edge 365 can extend around the bottom and sides of compression plate 300. For example, lower edge 365 can extend between top region 357 of left-side upper arm 321 and top region 358 of right-side upper arm 322 via a left side 367, a bottom side 366, and a right side 368 of compression plate 300. When viewed from the front, as in FIG. 3, lower edge 365 can have a curvilinear, convex shape, and upper edge 355 can have a curvilinear, concave shape. In several embodiments, lower edge 365 can connect with upper edge 355 at top region 357 of left-side upper arm 321 and at top region 358 of right-side upper arm 322. As shown in FIG. 3, upper edge 355 can be similar to upper edge 155 (FIG. 1), but which can have a more closed curvilinear shape extending around and back inward as it progresses upward from recess region 356 around notch 323 on each upper arm (e.g., 321, 322). For example, upper edge 355 can have an upsilon (ʊ) or an upside-down capital omega (Ω) shape. Generally, compression plate 300 can have a generally crescent shape, opening upward with the entrance of notch 323 at the top of compression plate 300.

In a number of embodiments, base portion 310 can have a height at the center of base portion 310 (e.g., at a vertical line extending between recess region 356 and bottom side 366) that is greater than the height of base portion 110 (FIG. 1), which can facilitate base portion 310 covering and/or applying pressure to a greater portion of the scrotum of the user. In some examples, base portion 310 can surround a majority of the scrotum of the user. In many embodiments, the distance between lower edge 365 and upper edge 355 can be greatest at the center of base portion 310 (e.g., at a vertical line extending between recess region 356 and bottom side 366), and can decrease gradually as lower edge 365 progresses upward around left side 367 and right side 368 up to top region 357 of left-side upper arm 321 and top region 258 of right-side upper arm 322, respectively. As shown in FIG. 3, the greatest width (e.g., horizontally between left side 367 and right side 368) of compression plate 330 can be at a region below recessed region 356. As shown in FIG. 3, the height of upper portion 320 and/or the upper arms (e.g., 321, 322), as measured by the vertical distance between recess region 356 at the bottom, and top region 357 or top region 358 at the top, can be greater than the height of base portion 310, as measured by the vertical distance between bottom side 366 and recess region 356.

As shown in FIGS. 3-4, compression plate 300 can be curved or angled inward toward inner surface 141, such that at least a portion of inner surface 141 is concave and/or at least a portion of outer surface 140 is convex. For example, base portion 310 can be curved and/or angled inward toward inner surface 141 at the center of base portion 310 along a vertical line extending between recess region 356 and bottom side 366), such that inner surface 341 is concave in the vertical direction, and such that recess region 356 and bottom side 366 of lower edge 365 are positioned rearward of an apex region 316 of base portion 310 located between recess region 356 and bottom side 366. Similarly, each of the upper arms (e.g., 321, 322) can be curved and/or angled inward toward inner surface 141 along any horizontal line extending between lower curve 365 and upper curve 355 on the upper arm (e.g., 321 or 322), such that inner surface 341 is concave in the horizontal direction. In many embodiments, such as shown at least partially in FIG. 4, the left and right sides (e.g., 367, 368) of lower edge 365 can be positioned further frontward than bottom side 366 of lower edge 365 and the top regions (e.g., 357, 358) of the upper arms (e.g., 321, 322).

The contouring, such as the curvature and/or angling of compression plate 300, and the curvilinear shape of upper edge 355 and lower edge 365, as described above, can permit compression plate 300 to generally conform to the anatomy of the user around the sides and underside of the base of the penis in the suprapubic region, including a substantial portion of the scrotum. In some example, bottom side 356 of lower edge 355 can be position along a bottom portion of the scrotum of the user. Based on the shape of upper edge 355, notch 325 can surround the penis of the user on at least a portion of the top of the base of the penis, which can facilitate securing compression plate 300 to the suprapubic region of the user such that a measurable, visible, or usable length of the penis is increased.

As shown in FIGS. 3-4, mounting holes 371-372 can be positioned at an upper region of base portion 310 on each side, and mounting holes 373-375 can be position at a lower region of base portion 310, such as adjacent to bottom side 366. In some example, mounting holes 371-372 can be used for straps that extend from mounting holes 371-372 frontward around the legs or hips of the user, or up to a belt at a positioned at the front of the user, and mounting holes 373, 374, and/or 375 can be used for straps that extend from the mounting holes (e.g., 373-375) rearward around the legs or hips of the user, or back to a belt at a position at the rear of the user. In other embodiments, other positions of the mounting holes can be used, and/or compression plate 300 can include another number of mounting holes, such as two holes, six holes, or another suitable number.

Figure 5:
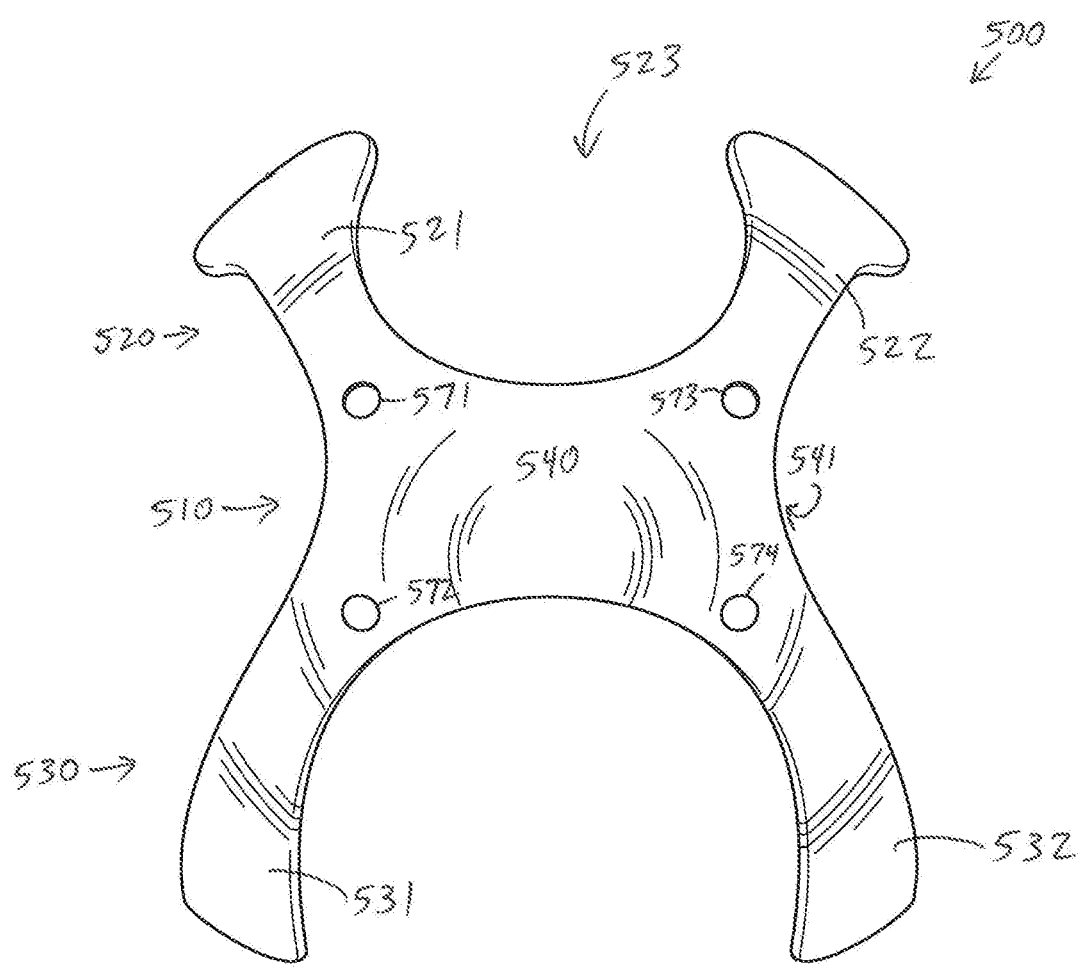
FIG. 5 illustrates a front view of a compression plate, according to another embodiment.
Figure 6:
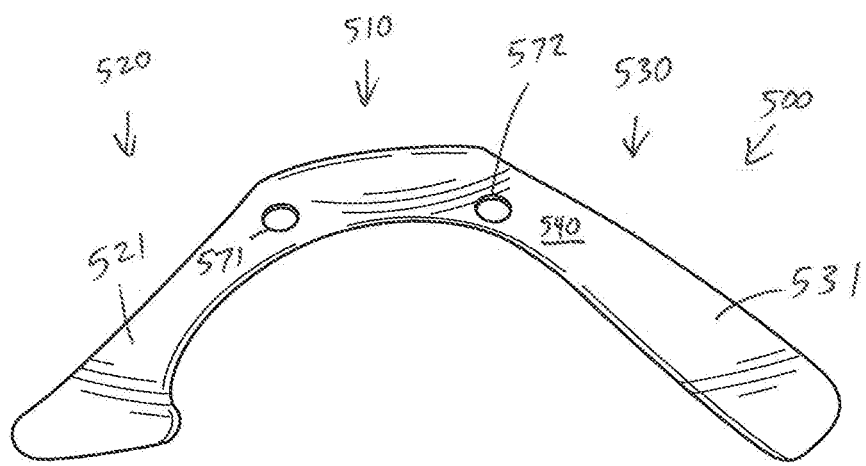
FIG. 6 illustrates a left side view of the compression plate of FIG. 5, in which the compression plate is rotated rearward (counterclockwise in FIG. 6) approximately 90 degrees.

Turning ahead in the drawings, FIG. 5 illustrates a front view of a compression plate 500. FIG. 6 illustrates a left side view of compression plate 500, in which compression plate 500 is rotated rearward (counterclockwise in FIG. 6) approximately 90 degrees. Compression plate 500 is merely exemplary, and embodiments of the compression plate are not limited to embodiments presented herein. The compression plate can be employed in many different embodiments or examples not specifically depicted or described herein. In some embodiments, compression plate 500 can be substantially similar to compression plate 100 (FIGS. 1-2), and various components of compression plate 500 can be similar or identical to various components of compression plate 100 (FIGS. 1-2). For example, compression plate 500 can include a base portion 510, an upper portion 520, and a lower portion 530, which can be similar to base portion 110

(FIG. 1), upper portion 120 (FIG. 1), and lower portion 130 (FIG. 1), respectively. Upper portion 520 can include a left-side upper arm 521, a right-side upper arm 522, and a notch 523 positioned between left-side upper arm 521 and right-side upper arm 522. Left-side upper arm 521, right-side upper arm 522, and notch 523 can be similar to left-side upper arm 121 (FIG. 1), right-side upper arm 122 (FIG. 1), and notch 123 (FIG. 1), respectively. Lower portion 530 can include a left-side lower arm 531 and a right side lower arm 532. Left-side lower arm 531 and right side lower arm 532 can be similar to left-side lower arm 131 (FIG. 1) and right side lower arm 132 (FIG. 1), respectively. Compression plate 500 can include an outer surface 540 and an inner surface 541 opposite outer surface 540. Outer surface 540 and inner surface 541 can be similar to outer surface 140 (FIG. 1) and inner surface 141 (FIG. 1), respectively. Compression plate 500 can include mounting holes 571-574, which can be similar to mounting holes 171-174 (FIG. 1).

Compression plate 500 can be different from compression plate 100 (FIG. 1) in some aspects. For example, as shown in FIG. 5, left-side upper arm 521 and right-side upper arm 522 can each be shorter than each of left-side lower arm 531 and right-side lower arm 532. Left-side upper arm 521, right-side upper arm 522, left-side lower arm 531, and right-side lower arm 532 can each be flared in a direction moving away from base portion 110 (e.g., when moving upward to the top ends of left-side upper arm 521 and right-side upper arm 522, and when moving downward to the bottom ends of left-side lower arm 531 and right-side lower arm 532). The top ends of left-side upper arm 521 and right-side upper arm 522, and the bottom ends of left-side lower arm 531 and right-side lower arm 532 can be substantially linear or slightly curvilinear. Each of the top ends of left-side upper arm 521 and right-side upper arm 522 can have a flared end with an elongated width relative to the rest of the arm (e.g., 521, 522). Mounting holes 571-574 can be positioned at base portion 510. Compression plate 500 can have a contoured shape similar to compression plate 100 (FIG. 1). Unlike compression plate 100 (FIG. 1), in which left-side lower arm 131 (FIG. 1) and right-side lower arm 132 (FIG. 1) have an orientation that extends further rearward than downward, with compression plate 500, left-side lower arm 531 and right-side lower arm 532 can have an orientation that extends further downward than rearward.

Figures 7, 8:
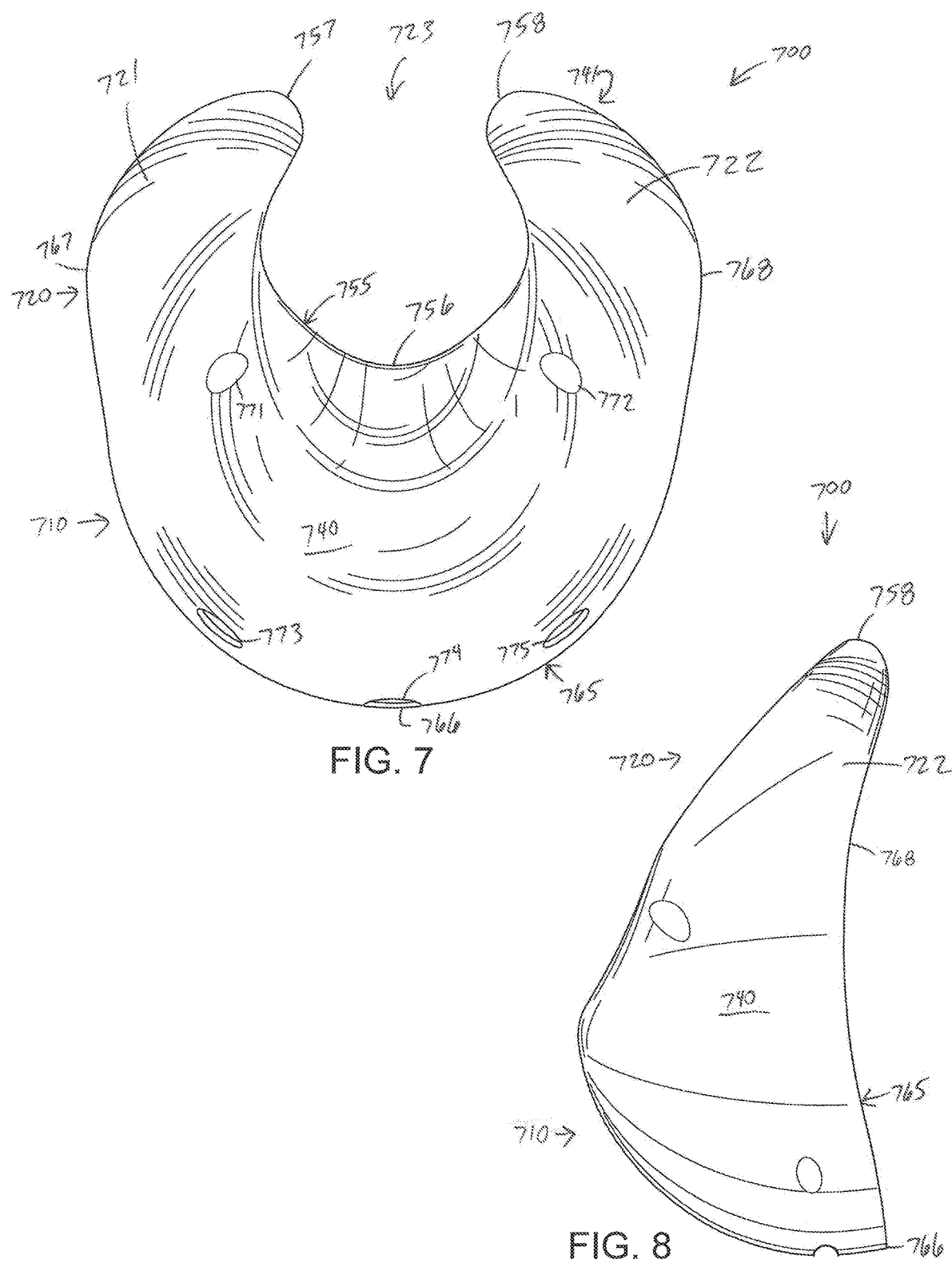
FIG. 7 illustrates a front view of a compression plate, according to another embodiment.
FIG. 8 illustrates a right side view of the compression plate of FIG. 7.

Turning ahead in the drawings, FIG. 7 illustrates a front view of a compression plate 700. FIG. 8 illustrates a right side view of compression plate 700. Compression plate 700 is merely exemplary, and embodiments of the compression plate are not limited to embodiments presented herein. The compression plate can be employed in many different embodiments or examples not specifically depicted or described herein. In some embodiments, compression plate 700 can be substantially similar to compression plate 300 (FIGS. 3-4), and various components and/or materials of compression plate 700 can be similar or identical to various components and/or materials of compression plate 300 (FIGS. 3-4). For example, compression plate 700 can include a base portion 710 and an upper portion 720, which can be similar to base portion 310 (FIG. 3) and upper portion 320 (FIG. 3), respectively. Upper portion 720 can include a left-side upper arm 721, a right-side upper arm 722, and a notch 723 positioned between left-side upper arm 721 and right-side upper arm 722. Left-side upper arm 721, right-side upper arm 722, and notch 723 can be similar to left-side upper arm 321 (FIG. 3), right-side upper arm 322 (FIG. 3), and notch 323 (FIG. 3), respectively. Compression plate 700 can include an outer surface 740 and an inner surface 741 opposite outer surface 740. Outer surface 740 and inner surface 741 can be similar to outer surface 340 (FIG. 3) and inner surface 341 (FIG. 3), respectively. Compression plate 700 can include an upper edge 755 and a lower edge 765. Upper edge 755 can be similar to upper edge 355 (FIG. 3), and lower edge 765 can be similar to lower edge 365 (FIG. 3). For example, upper edge 755 can extend between a top region 757 of left-side upper arm 721 and a top region 758 of right-side upper arm 722. Between top region 757 of left-side upper arm 721 and top region 758 of right-side upper arm 722, upper edge 755 can descend to a recess region 756. Lower edge 365 can extend between top region 757 of left-side upper arm 721 and top region 758 of right-side upper arm 722 via a left side 767, a bottom side 766, and a right side 768 of compression plate 700. Compression plate 700 can include mounting holes 771-775, which can be similar to mounting holes 371-375 (FIG. 3).

Compression plate 700 can be different from compression plate 300 (FIG. 3) in some aspects. For example, upper portion 720, left-side upper arm 721, and right-side upper arm 722 can be shorter than upper portion 320 (FIG. 3), left-side upper arm 321 (FIG. 3), and right-side upper arm 322 (FIG. 3), respectively. As shown in FIG. 7, the height of upper portion 720 and/or the upper arms (e.g., 721, 722), as measured by the vertical distance between recess region 756 at the bottom, and top region 757 or top region 758 at the top, can be less than the height of base portion 710, as measured by the vertical distance between bottom side 766 and recess region 756. Consequently, notch 723 can be more circular than the vertically elongated shape of notch 323 (FIG. 3). As shown in FIG. 7, the greatest width (e.g., horizontally between left side 767 and right side 768) of compression plate 700 can be at a region above recessed region 756, such that the upper arms (e.g., 721, 722) of compression plate 700 are wider than the upper arms (e.g., 321, 322 (FIG. 3)) of compression plate 300 (FIG. 3).

Figure 9:
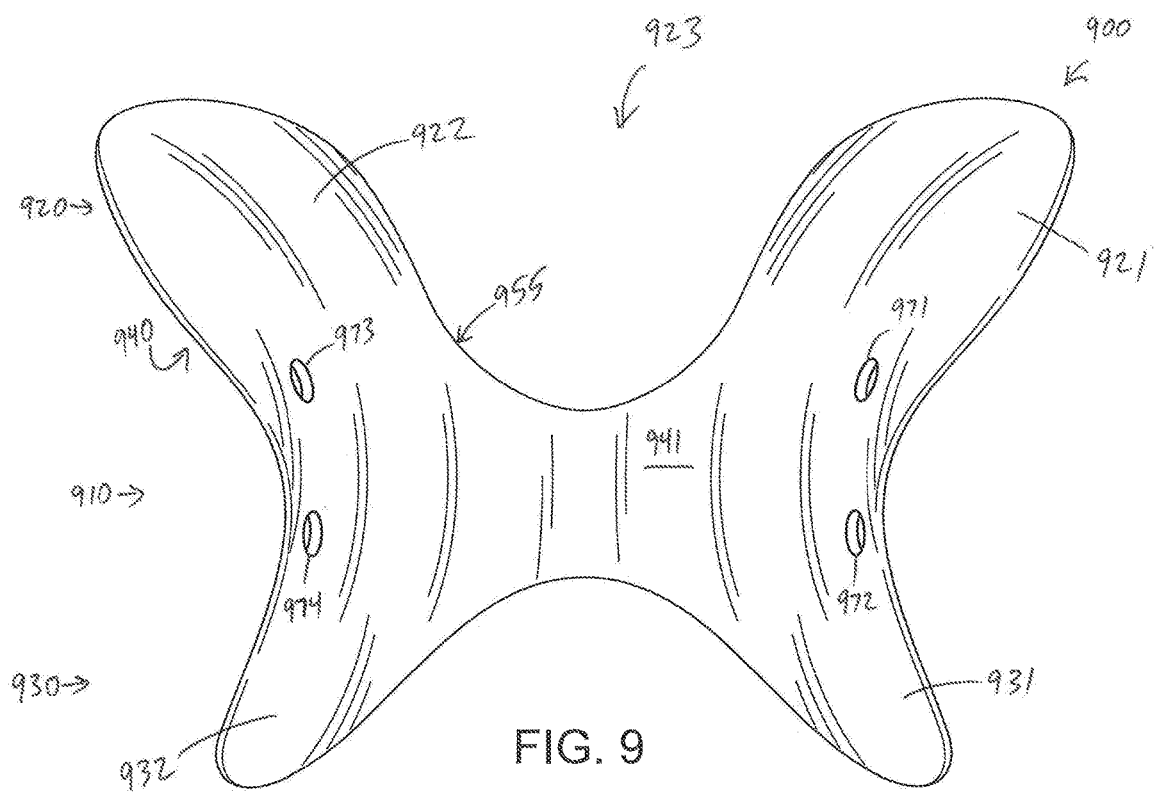
FIG. 9 illustrates a rear view of a compression plate, according to another embodiment.
Figure 10:
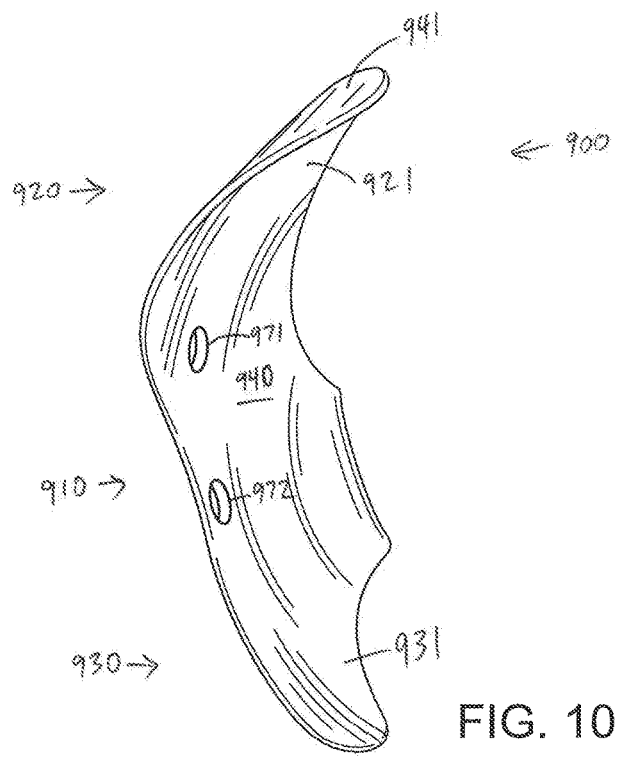
FIG. 10 illustrates a left side view of the compression plate of FIG. 9.

Turning ahead in the drawings, FIG. 9 illustrates a rear view of a compression plate 900. FIG. 10 illustrates a left side view of compression plate 900. Compression plate 900 is merely exemplary, and embodiments of the compression plate are not limited to embodiments presented herein. The compression plate can be employed in many different embodiments or examples not specifically depicted or described herein. In some embodiments, compression plate 900 can be substantially similar to compression plates 100 (FIGS. 1-2) and/or 500 (FIGS. 5-6), and various components and/or materials of compression plate 900 can be similar or identical to various components and/or materials of compression plates 100 (FIGS. 1-2) and/or 500 (FIGS. 5-6). For example, compression plate 900 can include a base portion 910, an upper portion 920, and a lower portion 930, which can be similar to base portions 110 (FIG. 1) and/or 510 (FIG. 5), upper portions 120 (FIG. 1) and/or 520 (FIG. 5), and lower portions 130 (FIG. 1) and/or 530 (FIG. 1), respectively. Upper portion 920 can include a left-side upper arm 921, a right-side upper arm 922, and a notch 923 positioned between left-side upper arm 921 and right-side upper arm 922. Left-side upper arm 921, right-side upper arm 922, and notch 923 can be similar to left-side upper arms 121 (FIG. 1) and/or 521 (FIG. 5), right-side upper arms 122 (FIG. 1) and/or 522 (FIG. 5), and notches 123 (FIG. 1) and/or 523 (FIG. 5), respectively. Lower portion 930 can include a left-side lower arm 931 and a right side lower arm 932. Left-side lower arm 931 and right side lower arm 932 can be similar to left-side lower arms 131 (FIG. 1) and/or 531 (FIG. 5), and right side lower arms 132 (FIG. 1) and/or 532 (FIG. 5), respectively. Compression plate 900 can include an outer surface 940 and an inner surface 941 opposite outer surface 940. Outer surface 940 and inner surface 941 can be similar to outer surfaces 140 (FIG. 1) and/or 540 (FIG. 5), and inner surfaces 141 (FIG. 1) and/or 541 (FIG. 1), respectively. Compression plate 900 can include mounting holes 971-974, which can be similar to mounting holes 171-174 (FIG. 1) and/or 571-574 (FIG. 5).

Compression plate 900 can be different from compression plate 100 (FIG. 1) and/or compression plate 500 (FIG. 5) in some aspects. For example, as shown in FIG. 9, compression plate 900 can have more of a butterfly shape, with left-side upper arm 921 and right-side upper arm 922 being generally longer and wider than left-side lower arm 931 and right side lower arm 932, and with left-side upper arm 921 right-side upper arm 922 extending further to the sides than left-side lower arm 931 and right side lower arm 932. Compression plate 900 can include an upper edge 955, which can be similar to upper edge 155 (FIG. 1), but which can have a more open curvilinear shape extending upward and outward to the side. Unlike upper edge 155 (FIG. 1), which curves around in a semicircular or horseshoe shape to achieve parallel lines on each upper arm (e.g., 121, 122 (FIG. 1)), upper edge 955 does not curve around sufficiently on each upper arm (e.g., 921, 922) to have parallel lines. Compression plate 900 can have a saddle surface shape, such that compression plate can be curved and/or angled inward toward inner surface 941 along a horizontal direction (e.g., inner surface 941 can be concave in a horizontal direction), and can be curved and/or angled outward toward outer surface 940 along a vertical direction (e.g., inner surface 941 can be convex in a vertical direction). Mounting holes 971-974 can be positioned at base portion 910, proximate to the sides of base portion 910.

Turning ahead in the drawings, FIG. 11 illustrates a front view of a compression plate 1100. FIG. 12 illustrates a right side view of compression plate 1100. Compression plate 1100 is merely exemplary, and embodiments of the compression plate are not limited to embodiments presented herein. The compression plate can be employed in many different embodiments or examples not specifically depicted or described herein. In some embodiments, compression plate 1100 can be substantially similar to compression plates 300 (FIGS. 3-4) and/or 700 (FIGS. 7-8), and various components and/or materials of compression plate 1100 can be similar or identical to various components and/or materials of compression plates 300 (FIGS. 1-2) and/or 700 (FIGS. 7-8). For example, compression plate 1100 can include a base portion 1110 and an upper portion 1120, which can be similar to base portions 310 (FIG. 3) and/or 710 (FIG. 7), and upper portion 320 (FIG. 3) and/or 720 (FIG. 7), respectively. Upper portion 1120 can include a left-side upper arm 1121, a right-side upper arm 1122, and a notch 1123 positioned between left-side upper arm 1121 and right-side upper arm 1122. Left-side upper arm 1121, right-side upper arm 1122, and notch 1123 can be similar to left-side upper arms 321 (FIG. 3) and/or 721 (FIG. 7), right-side upper arms 322 (FIG. 3) and/or 722 (FIG. 7), and notches 323 (FIG. 3) and/or 723 (FIG. 7), respectively. Compression plate 1100 can include an outer surface 1140 and an inner surface 1141 opposite outer surface 1140. Outer surface 1140 and inner surface 1141 can be similar to outer surfaces 340 (FIG. 3) and/or 740 (FIG. 7), and inner surfaces 341 (FIG. 3) and/or 741 (FIG. 7), respectively. Compression plate 1100 can include an upper edge 1155 and a lower edge 1165. Upper edge 1155 can be similar to upper edges 355 (FIG. 3) and/or 755 (FIG. 7), and lower edge 1165 can be similar to lower edges 365 (FIG. 3) and/or 756 (FIG. 3). Compression plate 1100 can include mounting holes 1171-1173, which can be similar to mounting holes 371, 372, and 374 (FIG. 3).

Compression plate 1100 can be different from compression plates 300 (FIG. 3) and/or 700 (FIG. 7) in some aspects. For example, compression plate 1100 can be generally shaped as a bunny rabbit's head and ears, with base portion 1110 being shaped as the bunny rabbit's head and upper portion 1120 being shaped as the bunny rabbit's ears. As shown in FIGS. 11-12, upper arms 1121 and 1122 can be tabs that extend upward from base portion 1110. For example, left-side upper arm 1121 can extend upward to a top region 1157 of left-side upper arm 1121 from base portion 1110 at a base of left-side upper arm 1121 that extends between an outer base 1126 and an inner base 1128 of left-side upper arm 1121. Similarly, right-side upper arm 1122 can extend upward to a top region 1158 of right-side upper arm 1122 from base portion 1110 at a base of right-side upper arm 1122 that extends between an outer base 1127 and an inner base 1129 of right-side upper arm 1122. Upper edge 1155 can extend between outer base 1126 of left-side upper arm 1121 and outer base 1127 of right-side upper arm 1122. Between outer base 1126 of left-side upper arm 1121 and outer base 1127 of right-side upper arm 1122, upper edge 1155 can ascend upward and outward, and then upward and inward, in each case, to a top region 1157 of left-side upper arm 1121 and a top region 1158 of right-side upper arm 1122. Between top region 1157 of left-side upper arm 1121 and a top region 1158 of right-side upper arm 1122, upper edge 1155 can descend downward and inward, and then downward in outward, in each case, to inner base 1128 of left-side upper arm 1121 and inner base 1129 of right-side upper arm 1122. Between inner base 1128 of left-side upper arm 1121 and inner base 1129 of right-side upper arm 1122, upper edge 1155 can extend downward, inward, and frontward, to a recess region 1156 of base portion 1110. Lower edge 1165 can extend between outer base 1126 of left-side upper arm 1121 and outer base 1127 of right-side upper arm 1122 via a left side 1167, a bottom side 1166, and a right side 1168 of compression plate 1100.

In some embodiments, a lower portion (e.g., 1224) of the upper arms (e.g., 1121-1122) can be angled outward toward outer surface 1140 with respect to base portion 110, such that the lower portion (e.g., 1224) of the upper arms (e.g., 1121-1122) can extend upward and slightly frontward, as shown in FIG. 12. An upper portion (e.g., 1225) of the upper arms (e.g., 1121-1122) can be angled inward toward inner surface 1141 with respect to the lower portion (e.g., 1224) of the upper arms (e.g., 1121-1122), such that the upper portion (e.g., 1225) of the upper arms (e.g., 1121-1122) can extend upward and slightly rearward.

Figure 13:
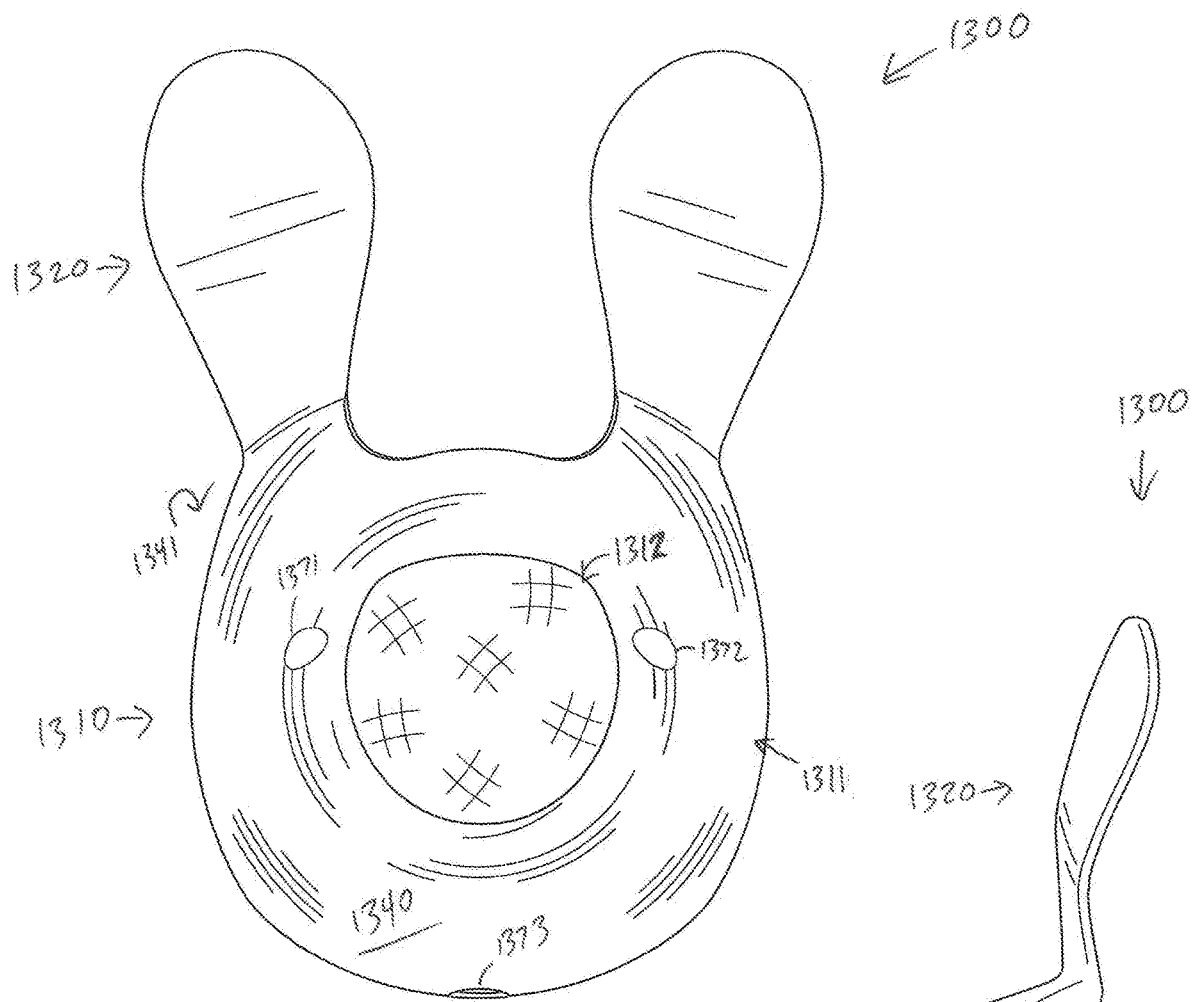
FIG. 13 illustrates a front view of a compression plate, according to another embodiment.
Figure 14:
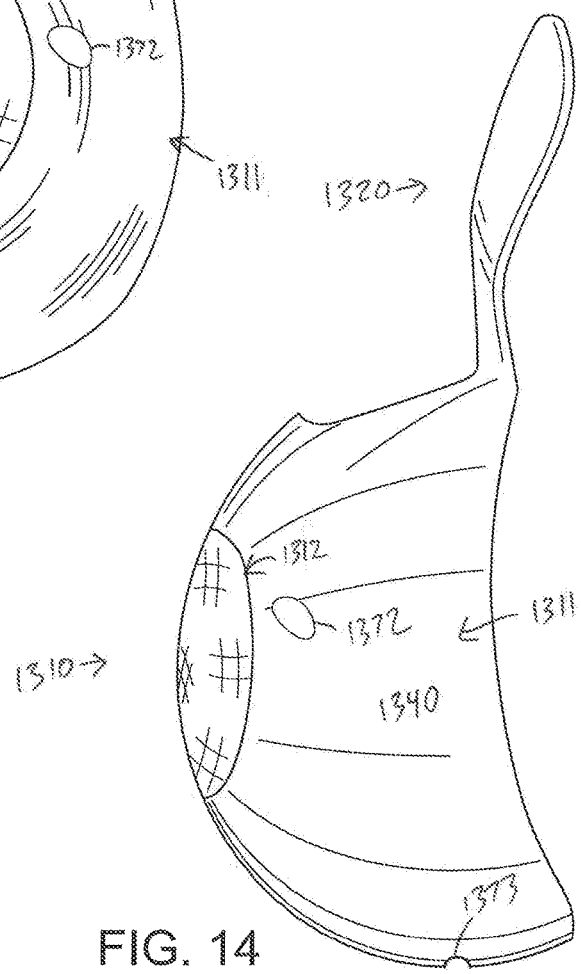
FIG. 14 illustrates a right side view of the compression plate of FIG. 13.

Turning ahead in the drawings, FIG. 13 illustrates a front view of a compression plate 1300. FIG. 14 illustrates a right side view of compression plate 1300. Compression plate 1300 is merely exemplary, and embodiments of the compression plate are not limited to embodiments presented herein. The compression plate can be employed in many different embodiments or examples not specifically depicted or described herein. In some embodiments, compression plate 1300 can be substantially similar to compression plate 1100 (FIGS. 11-12), and various components and/or materials of compression plate 1300 can be similar or identical to various components and/or materials of compression plate 1100 (FIGS. 11-12). For example, compression plate 1300 can include a base portion 1310 and an upper portion 1320. Upper portion 1320 can be similar or identical to upper portion 1120 (FIG. 11). Base portion 1310 can be similar to base portion 1110 (FIG. 11). Compression plate 1300 can include an outer surface 1340 and an inner surface 1341 opposite outer surface 1340. Outer surface 1340 and inner surface 1341 can be similar to outer surface 1140 (FIG. 11) and inner surface 1141 (FIG. 11), respectively. Compression plate 1300 can include mounting holes 1371-1373, which can be similar to mounting holes 1171-1173 (FIG. 11).

Compression plate 1300 can be different from compression plate 1100 (FIG. 11) in some aspects. For example, base portion 13109 can include a first region 1311 and a second region 1312. First region 1311 can surround second region 1312. First region 1311 can be made of a first material, such as a rigid or semi-rigid material, as described above with respect to compression plate 100 (FIG. 1). Second region 1312 can be made of a second material that is different from the first material. In some embodiments, the second material can be a mesh or breathable fabric. In other embodiments, the second material can be a different rigid or semi-rigid material. In some embodiments, second region 1312 can be centered on base portion 1310, and can be shaped to appear like a nose of the bunny rabbit's head.

Figure 15:
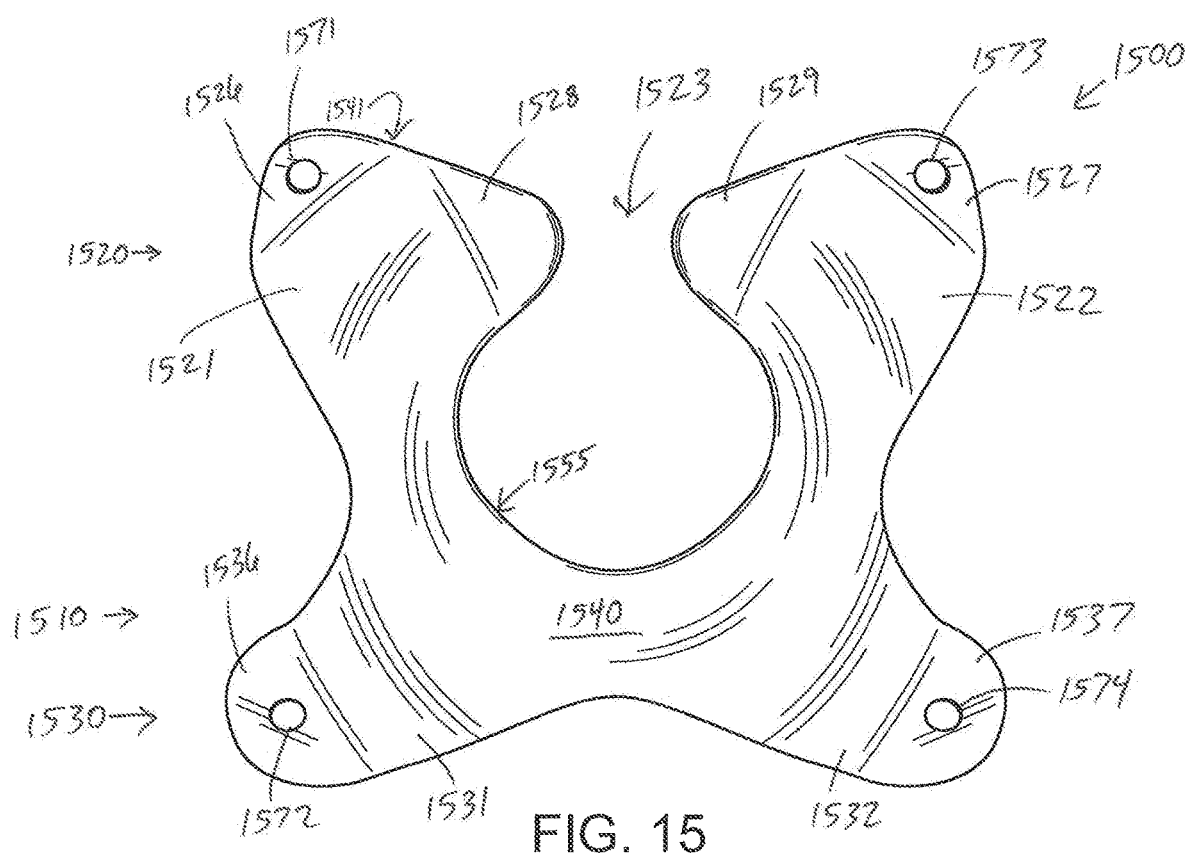
FIG. 15 illustrates a front view of a compression plate, according to another embodiment.
Figure 16:
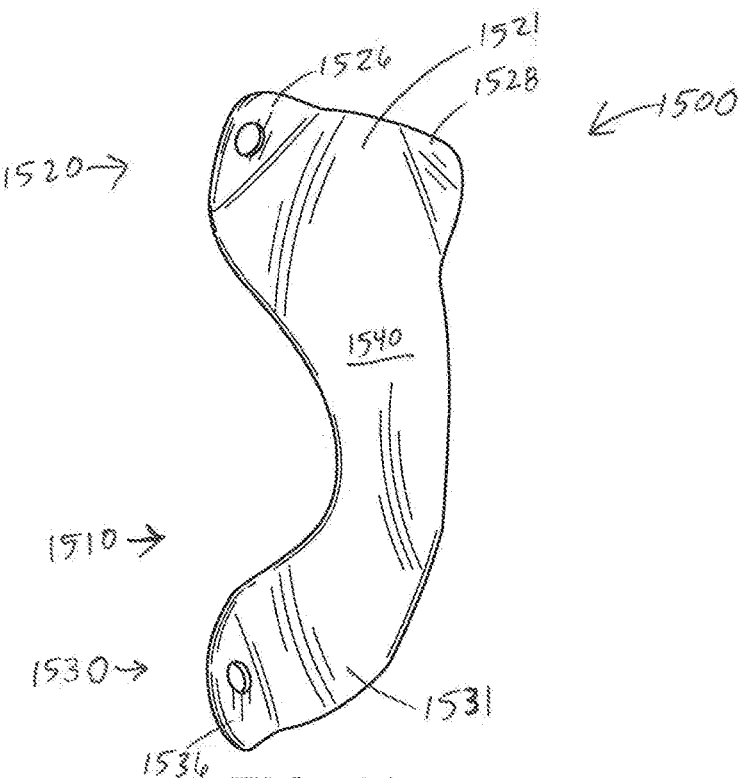
FIG. 16 illustrates a left side view of the compression plate of FIG. 15.

Turning ahead in the drawings, FIG. 15 illustrates a front view of a compression plate 1500. FIG. 16 illustrates a left side view of compression plate 1500. Compression plate 1500 is merely exemplary, and embodiments of the compression plate are not limited to embodiments presented herein. The compression plate can be employed in many different embodiments or examples not specifically depicted or described herein. In some embodiments, compression plate 1500 can be substantially similar to compression plate 100 (FIGS. 1-2), compression plate 500 (FIGS. 5-6), and/or compression plate 900 (FIGS. 9-10), and various components and/or materials of compression plate 1500 can be similar or identical to various components and/or materials of compression plate 100 (FIGS. 1-2), compression plate 500 (FIGS. 5-6), and/or compression plate 900 (FIGS. 9-10). For example, compression plate 1500 can include a base portion 1510, an upper portion 1520, and a lower portion 1530, which can be similar to base portions 110 (FIG. 1), 510 (FIG. 5), and/or 910 (FIG. 9), upper portions 120 (FIG. 1), 520 (FIG. 5), and/or 920 (FIG. 9), and lower portions 130 (FIG. 1), 530 (FIG. 1), and/or 930 (FIG. 9), respectively. Upper portion 1520 can include a left-side upper arm 1521, a right-side upper arm 1522, and a notch 1523 positioned between left-side upper arm 1521 and right-side upper arm 1522. Left-side upper arm 1521, right-side upper arm 1522, and notch 1523 can be similar to left-side upper arms 121 (FIG. 1), 521 (FIG. 5), and/or 921 (FIG. 9), right-side upper arms 122 (FIG. 1), 522 (FIG. 5), and/or 922 (FIG. 9), and notches 123 (FIG. 1), 523 (FIG. 5), and/or 923 (FIG. 9), respectively. Lower portion 1530 can include a left-side lower arm 1531 and a right side lower arm 1532. Left-side lower arm 1531 and right side lower arm 1532 can be similar to left-side lower arms 131 (FIG. 1), 531 (FIG. 5), and/or 931 (FIG. 9), and right side lower arms 132 (FIG. 1), 532 (FIG. 5), and/or 932 (FIG. 9), respectively. Compression plate 1500 can include an outer surface 1540 and an inner surface 1541 opposite outer surface 1540. Outer surface 1540 and inner surface 1541 can be similar to outer surfaces 140 (FIG. 1), 540 (FIG. 5), and/or 940 (FIG. 9), and inner surfaces 141 (FIG. 1), 541 (FIG. 5), and/or 941 (FIG. 9), respectively. Compression plate 900 can include mounting holes 1571-1574, which can be similar to mounting holes 171-174 (FIG. 1), 571-574 (FIG. 5), and/or 971-974 (FIG. 9).

Compression plate 1500 can be different from compression plate 100 (FIG. 1), compression plate 500 (FIG. 5), and/or compression plate 900 (FIG. 9) in some aspects. For example, as shown in FIG. 15, compression plate 1500 can include an upper edge 1555, which can be similar to upper edge 155 (FIG. 1), but which can have a more closed curvilinear shape extending around and back inward as it progresses upward around notch 1523 on each upper arm (e.g., 1521, 1522) before again opening outward. For example, upper edge 1555 can have an upsilon (ʊ) or an upside-down capital omega (Ω) shape. Based on the shape of upper edge 1555, notch 1525 can surround the penis of the user on at least a portion of the top of the base of the penis, which can facilitate securing compression plate 1500 to the suprapubic region of the user. Like compression plate 100 (FIG. 1), compression plate 1500 can be curved or angled inward toward inner surface 1541 such that inner surface 141 is concave in both a vertical and horizontal direction, except that compression plate 1500 can include tabs 1526 and 1528 on left-side upper arm 1521, tabs 1527 and 1529 on right-side upper arm 1522, tab 1536 on left-side lower arm 1531, and tab 1537 on left-side lower arm 1532, which can be angled outward toward outer surface 1540 with respect to the rest of the arm (e.g., 1521, 1522, 1531, or 1532). For example, tabs 1528 and 1529 can be positioned at the inner (adjacent to notch 1523), top region of left-side upper arm 1521 and right-side upper arm 1522, respectively, and can be angled outward toward surface 1540 with respect to the surrounding portions of left-side upper arm 1521 and right-side upper arm 1522, respectively. Similarly, tabs 1526 and 1527 can be positioned at the outer (opposite of notch 1523), top region of left-side upper arm 1521 and right-side upper arm 1522, respectively, and can be angled outward toward surface 1540 with respect to the surrounding portions of left-side upper arm 1521 and right-side upper arm 1522, respectively. Additionally, tabs 1536 and 1537 can be positioned at the outer, bottom region of left-side lower arm 1531 and right-side lower arm 1532, respectively, and can be angled outward toward surface 1540 with respect to the surrounding portions of left-side lower arm 1531 and right-side lower arm 1532, respectively. In some embodiments, tabs 1526, 1527, 1528, 1529, 1536, and/or 1537 can be angled outward to prevent the corners of compression plate 1500 from curving toward the suprapubic region of the user, which can increase comfort for the user while compression plate 1500 compresses the suprapubic region of the user. Mounting hole 1571 can be positioned at tab 1526, mounting hole 1572 can be positioned at tab 1536, mounting hole 1573 can be positioned at tab 1527, and mounting hole 1574 can be positioned at tab 1537.

Figure 17:
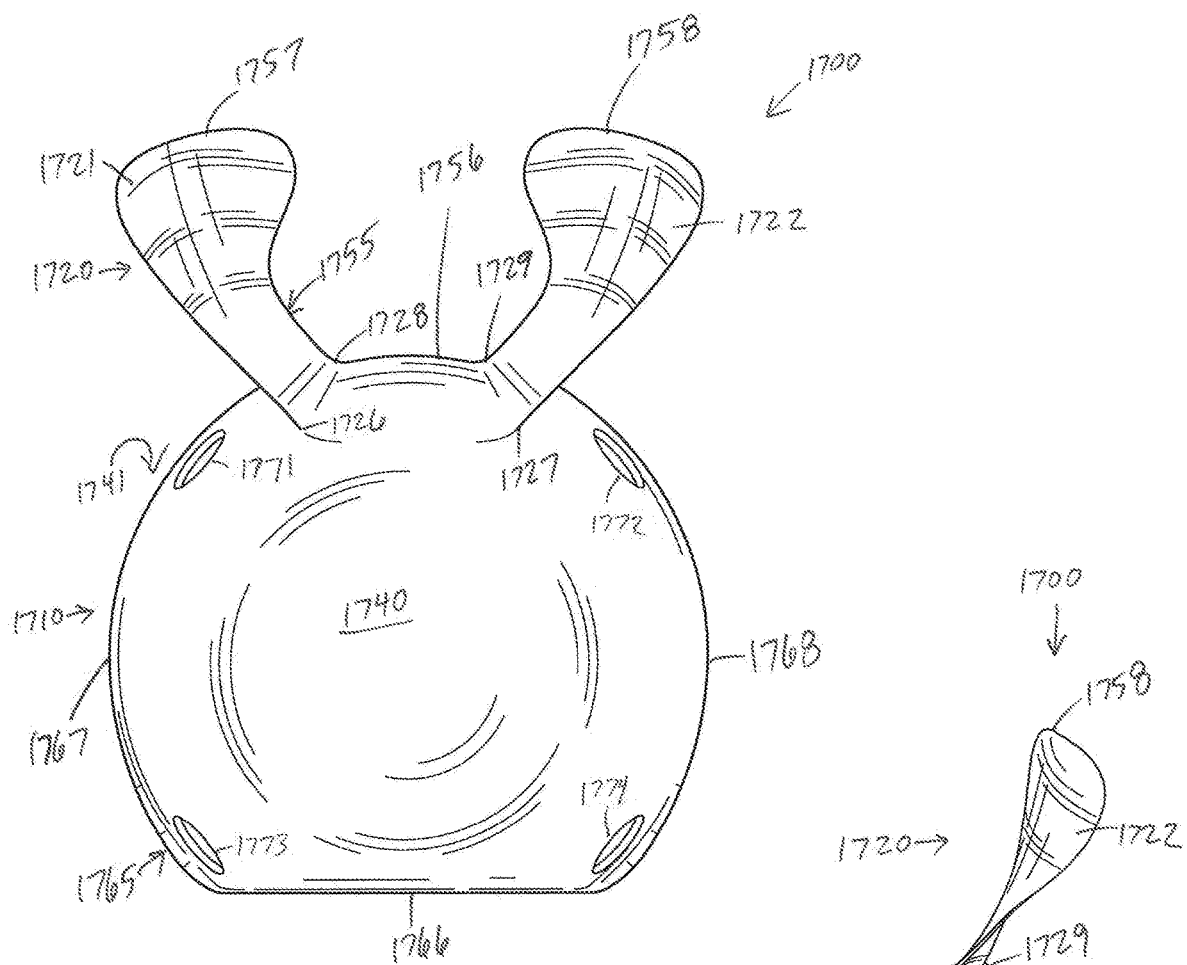
FIG. 17 illustrates a front view of a compression plate, according to another embodiment.
Figure 18:
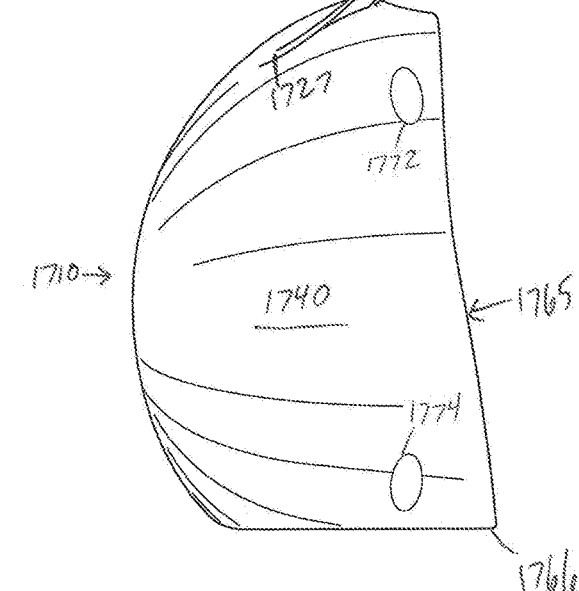
FIG. 18 illustrates a right side view of the compression plate of FIG. 17.

Turning ahead in the drawings, FIG. 17 illustrates a front view of a compression plate 1700. FIG. 18 illustrates a right side view of compression plate 1700. Compression plate 1700 is merely exemplary, and embodiments of the compression plate are not limited to embodiments presented herein. The compression plate can be employed in many different embodiments or examples not specifically depicted or described herein. In some embodiments, compression plate 1700 can be substantially similar to compression plate 1100 (FIGS. 11-12), and various components and/or materials of compression plate 1700 can be similar or identical to various components and/or materials of compression plate 1100 (FIGS. 11-12). For example, compression plate 1700 can include a base portion 1710 and an upper portion 1720. Upper portion 1710 can be similar to upper portion 1120 (FIG. 11). Base portion 1710 can be similar to base portion 1110 (FIG. 11). Compression plate 1700 can include an outer surface 1740 and an inner surface 1741 opposite outer surface 1740. Outer surface 1740 and inner surface 1741 can be similar to outer surface 1140 (FIG. 11) and inner surface 1141 (FIG. 11), respectively. Compression plate 1700 can include an upper edge 1755 and a lower edge 1765. Upper edge 1755 can be similar to upper edge 1155 (FIG. 11), and lower edge 1765 can be similar to lower edge 1165 (FIG. 11). Compression plate 1700 can include mounting holes 1771-1774, which can be similar to mounting holes 1171-1173 (FIG. 11), and/or 371, 372, 373, and 375 (FIG. 3).

Compression plate 1700 can be different from compression plate 1100 (FIG. 11) in some aspects. As shown in FIGS. 17-18, upper arms 1721 and 1722 can be tabs that extend upward, outward, and rearward from base portion 1710. For example, left-side upper arm 1721 can extend upward, outward, and rearward to a top region 1757 of left-side upper arm 1721 from base portion 1710 at a base of left-side upper arm 1721 that extends between an outer base 1726 and an inner base 1728 of left-side upper arm 1721. Similarly, right-side upper arm 1722 can extend upward, outward, and rearward to a top region 1758 of right-side upper arm 1722 from base portion 1710 at a base of right-side upper arm 1722 that extends between an outer base 1727 and an inner base 1729 of right-side upper arm 1122. Upper edge 1755 can extend between outer base 1726 of left-side upper arm 1721 and outer base 1727 of right-side upper arm 1722. Between outer base 1726 of left-side upper arm 1721 and outer base 1727 of right-side upper arm 1722, upper edge 1755 can ascend upward, outward, and rearward, in each case, to a top region 1757 of left-side upper arm 1721 and a top region 1758 of right-side upper arm 1722. Top region 1757 of left-side upper arm 1721 and a top region 1758 of right-side upper arm 1722 can be substantially flat, but extend rearward as upper edge 1755 moves inward, in each case. Between top region 1757 of left-side upper arm 1721 and a top region 1758 of right-side upper arm 1722, upper edge 1755 can descend downward, outward, and frontward, and then downward, inward, and frontward, in each case, to inner base 1728 of left-side upper arm 1721 and inner base 1729 of right-side upper arm 1722. Between inner base 1728 of left-side upper arm 1721 and inner base 1729 of right-side upper arm 1722, upper edge 1755 can extend across a recess region 1156 of base portion 1710. Outer bases 1726 and 1727 can be positioned frontward of inner bases 1728 and 1729. Lower edge 1765 can extend between outer base 1726 of left-side upper arm 1721 and outer base 1727 of right-side upper arm 1722 via a left side 1767, a bottom side 1766, and a right side 1768 of compression plate 1700. In many embodiments, bottom side 1766 can be substantially flat to a width that is greater than more than half of the width between left side 1767 and right side 1768

In use, the user can don the compression plate as described above, such as in part of a compression assembly, as described above, by wrapping the belt, harness, or straps around his waist or hips such that the inner surface of the compression plate engages the suprapubic region of the user. The penis of the user can be in the notch to provide maximum coverage and compression of the suprapubic region. The compression plate can be positioned such that the recess region at the bottom of the notch engages the penis, although this is not required. The user can pull the belt, harness, or straps taut to urge the compression plate against the suprapubic region to compress the suprapubic region. The contours of the compression plate angling or curving inward toward the user permits the compression plate to better conform to the anatomy of the user, while also providing maximum compression of the suprapubic region. The compression plate can be a rigid structure that applies pressure to the pubic area below and to the sides of the penis at the base of the penis through force applied by tension from the belt, harness, straps, or customized garment. The compression plate thus compresses the suprapubic region to increase the measurable, visible, or usable length of the penis of the user. The compression plate therefore simulates the effects of a suprapubic fat pad reduction surgery without the expense, pain, and recovery time of the surgery.

Having described the invention in detail, it will be apparent that modifications and variations are possible without departing from the scope of the invention defined in the appended claims.

When introducing elements of the present invention or the illustrated embodiments thereof, the articles "a," "an," "the," and "said" are intended to mean that there are one or more of the elements. The terms "comprising," "including," and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense. It is understood that any feature of any embodiment described above may be combined with any other suitable feature(s) of any other embodiment(s).

What is claimed is:

1. A compression plate for compressing a suprapubic region of a user, the compression plate comprising:
 a base portion;
 an upper portion positioned above the base portion, the upper portion comprising a left-side upper arm, a right-side upper arm, and a notch positioned between the left- and right-side upper arms, and the notch being configured to receive a penis of the user;
 an inner surface; and
 an outer surface opposite the inner surface,
wherein:
 the upper portion is contoured to apply pressure to and compress at least a portion of the suprapubic region of the user such that a measurable, visible, or usable length of the penis is increased; and
 at least a portion of each of the left- and right-side upper arms are curved or angled inward toward the inner surface relative to the base portion.

2. The compression plate of claim 1, wherein:
 the left- and right-side upper arms are configured to apply pressure to and compress a portion of the suprapubic region of the user at a left side and a right side of a base of the penis; and
 the base portion is configured to apply pressure to and compress a portion of a scrotum of the user at an underside below the base of the penis.

3. The compression plate of claim 1, wherein the base portion is configured to apply pressure to and compress at least a portion of a scrotum of the user.

4. The compression plate of claim 1, wherein the inner surface is concave with respect to the compression plate.

5. The compression plate of claim 1, wherein the compression plate is rigid.

6. The compression plate of claim 1, wherein the base portion comprises a first region having a first material and a second region having a second material that is different from the first material.

7. The compression plate of claim 6, wherein the first region surrounds the second region.

8. The compression plate of claim 6, wherein the second material is a mesh or breathable fabric.

9. The compression plate of claim 1 further comprising at least one mounting hole.

10. A compression assembly comprising:
the compression plate of claim 9; and
a belt configured to urge the compression plate toward the user to compress the suprapubic region of the user, the belt being configured to engage with the at least one mounting hole.

11. A compression plate for compressing a suprapubic region of a user, the compression plate comprising:
a base portion;
an upper portion positioned above the base portion, the upper portion comprising a left-side upper arm, a right-side upper arm, and a notch positioned between the left- and right-side upper arms, and the notch being configured to receive a penis of the user; and
a lower portion below the base portion, the lower portion comprising a left-side lower arm and a right side lower arm each extending below the base portion,
wherein:
the upper portion is contoured to apply pressure to and compress at least a portion of the suprapubic region of the user such that a measurable, visible, or usable length of the penis is increased.

12. The compression plate of claim 11, wherein the base portion is narrower in width than at least a portion of the upper portion and at least a portion of the lower portion.

13. The compression plate of claim 11 further comprising:
an inner surface; and
an outer surface opposite the inner surface,
wherein:
at least a portion of each of the left- and right-side upper arms and the left- and right-side lower arms are curved or angled inward toward the inner surface relative to the base portion.

14. A method of providing a compression plate for compressing a suprapubic region of a user, the method comprising:
providing a base portion;
providing an upper portion positioned above the base portion, the upper portion comprising a left-side upper arm, a right-side upper arm, and a notch positioned between the left- and right-side upper arms, and the notch being configured to receive a penis of the user; and
providing a lower portion below the base portion, the lower portion comprising a left-side lower arm and a right side lower arm each extending below the base portion,
wherein:
the upper portion is contoured to apply pressure to and compress at least a portion of the suprapubic region of the user such that a measurable, visible, or usable length of the penis is increased.

15. The method of claim 14, wherein the base portion is configured to apply pressure to and compress at least a portion of a scrotum of the user.

16. The method of claim 14, wherein the base portion comprises a first region having a first material and a second region having a second material that is different from the first material.

* * * * *